US009670478B2

(12) United States Patent
Yamamoto et al.

(10) Patent No.: US 9,670,478 B2
(45) Date of Patent: Jun. 6, 2017

(54) METHOD FOR MODIFYING NUCLEIC ACIDS

(71) Applicant: TAKARA BIO INC., Shiga (JP)

(72) Inventors: Junko Yamamoto, Shiga (JP); Keiko Kubo, Shiga (JP); Takashi Uemori, Shiga (JP); Hiroyuki Mukai, Shiga (JP); Kiyozo Asada, Shiga (JP)

(73) Assignee: TAKARA BIO INC., Shiga (JP)

( * ) Notice: Subject to any disclaimer, the term of this patent is extended or adjusted under 35 U.S.C. 154(b) by 0 days.

(21) Appl. No.: 15/252,663

(22) Filed: Aug. 31, 2016

(65) Prior Publication Data

US 2016/0362676 A1 Dec. 15, 2016

Related U.S. Application Data

(62) Division of application No. 13/980,970, filed as application No. PCT/JP2012/051230 on Jan. 20, 2012, now Pat. No. 9,458,498.

(30) Foreign Application Priority Data

Jan. 24, 2011 (JP) .................. 2011-012363
Jan. 24, 2011 (JP) .................. 2011-012372

(51) Int. Cl.
*C12N 15/01* (2006.01)
*C12Q 1/68* (2006.01)

(52) U.S. Cl.
CPC ............. *C12N 15/01* (2013.01); *C12Q 1/686* (2013.01); *C12Q 1/689* (2013.01); *C12Q 1/6848* (2013.01)

(58) Field of Classification Search
None
See application file for complete search history.

(56) References Cited

U.S. PATENT DOCUMENTS

| | | | | |
|---|---|---|---|---|
| 4,302,204 A | * | 11/1981 | Wahl | ................ C12N 15/1034 422/504 |
| 4,321,919 A | * | 3/1982 | Edelson | ............... A61M 1/3681 128/898 |
| 2009/0098613 A1 | | 4/2009 | Asada et al. | |
| 2009/0305240 A1 | | 12/2009 | Yoshida et al. | |
| 2010/0170777 A1 | | 7/2010 | Yoshida et al. | |
| 2011/0053790 A1 | | 3/2011 | Yoshida et al. | |
| 2012/0122082 A1 | * | 5/2012 | Soejima | ............... C12Q 1/6848 435/5 |

FOREIGN PATENT DOCUMENTS

| | | |
|---|---|---|
| JP | 4127847 | 5/2008 |
| JP | 2008-137962 | 6/2008 |
| WO | 2005/001469 | 1/2005 |
| WO | 2009/022558 | 2/2009 |

OTHER PUBLICATIONS

Jinno Y, Yoshiura K, Niikawa N. Use of psoralen as extinguisher of contaminated DNA in PCR. Nucleic Acids Res. Nov. 25, 1990; 18(22):6739.*
Linhardt, R.J., Al-Hakim, A. and Liu, J., Acidic polysaccharides: their modification and potential uses. In Biotechnology and Polymers, Springer US, 1991, pp. 155-165.*
Parshionikar S, Laseke I, Fout GS. Use of propidium monoazide in reverse transcriptase PCR to distinguish between infectious and noninfectious enteric viruses in water samples. Appl Environ Microbiol. Jul. 2010; 76(13):4318-26.*
Ruponen M, Rönkkö S, Honkakoski P, Pelkonen J, Tammi M, Urtti A. Extracellular glycosaminoglycans modify cellular trafficking of lipoplexes and polyplexes. J Biol Chem. Sep. 7, 2001; 276(36):33875-80.*
Sogo, J.M., Ness, P.J., Widmer, R.M., Parish, R.W. and Koller, T., 1984. Psoralen-crosslinking of DNA as a probe for the structure of active nucleolar chromatin. Journal of molecular biology, 178(4), pp. 897-919.*
International Search Report issued Mar. 13, 2012, in International (PCT) Application No. PCT/JP2012/051230.
International Preliminary Report on Patentability issued Jul. 30, 2013, and English translation of Written Opinion of the International Searching Authority issued Mar. 13, 2012, in International (PCT) Application No. PCT/JP2012/051230.
Nocker et at, "Selective Removal of DNA from Dead Cells of Mixed Bacterial Communities by Use of Ethidium Monoazide", Applied and Environmental Microbiology, vol. 72, No. 3, Mar. 2006, pp. 1997-2004.
Nocker et al., "Comparison of propidium monoazide with ethidium monoazide for differentiation of live vs. dead bacteria by selective removal of DNA from dead cells", Journal of Microbiological Methods, vol. 67, 2006, pp. 310-320.
Cimino et al., "Post-PCR sterilization: a method to control carryover contamination for the polymerase chain reaction", Nucleic Acids Research, vol. 19, No. 1, 1991, pp. 99-107.
Pan et al., "Enumeration of Viable Listeria monocytogenes Cells by Real-Time PCR with Propidium Monoazide and Ethidium Monoazide in the Presence of Dead Cells", Applied and Environmental Microbiology, vol. 73, No. 24, Dec. 2007, pp. 8028-8031.

(Continued)

*Primary Examiner* — Angela M Bertagna
*Assistant Examiner* — Olayinka Oyeyemi
(74) *Attorney, Agent, or Firm* — Wenderoth, Lind & Ponack, L.L.P.

(57) ABSTRACT

The present invention pertains to a method for modifying a nucleic acid contained in a sample comprising a step for bringing the sample into contact with a nucleic acid-modifying agent in the presence of an acidic polysaccharide and/or a nucleotide; and a method for selectively detecting a nucleic acid derived from living cells contained in the sample, comprising the following steps: (a) a step for modifying a nucleic acid contained in a sample according to the method for modifying a nucleic acid contained in a sample, which includes a step for bringing the sample into contact with a nucleic acid-modifying agent in the presence of an acidic polysaccharide and/or a nucleotide; and (b) a step for selectively detecting an unmodified nucleic acid from the sample after step (a). The present invention further pertains to a kit and composition for use in these methods.

1 Claim, No Drawings

(56) References Cited

OTHER PUBLICATIONS

Chinese Office Action and Search Report dated May 5, 2014, issued in corresponding Chinese Patent Application No. 201280014786.1. (with English translation).
Extended European Search Report issued Aug. 4, 2014, in corresponding European Patent Application No. 12739127.4.
Korean Office Action dated Sep. 10, 2015, issued in corresponding Korean Patent Application No. 10-2013-7021390 (with English translation).
Sogo et al., "The use of psoralen-photocrosslinking for the analysis of the chromatin structure during transcription", In Photochemical probes in biochemistry, 1989, pp. 179-194, Springer Netherlands.
Capela et al., "Effect of homogenisation on bead size and survival of encapsulated probiotic bacteria", Food Research International, 2007, vol. 40, No. 10, pp. 1261-1269.
Chan et al., "Bioencapsulation by compression coating of probiotic bacteria for their protection in an acidic medium", Process Biochemistry, 2005, vol. 40, No. 10, pp. 3346-3351.
Douglas et al., "Effects of alginate inclusion on the vector properties of chitosan-based nanoparticles", J. Control Release, 2006, vol. 115, No. 3, pp. 354-361.

* cited by examiner

```
SEQUENCE LISTING

<160> NUMBER OF SEQ ID NOS: 5

<210> SEQ ID NO 1
<211> LENGTH: 20
<212> TYPE: DNA
<213> ORGANISM: Artificial
<220> FEATURE:
<223> OTHER INFORMATION: Nucleotide sequence of LacZ-F

<400> SEQUENCE: 1
cctgaggccg atactgtcgt                                            20

<210> SEQ ID NO 2
<211> LENGTH: 18
<212> TYPE: DNA
<213> ORGANISM: Artificial
<220> FEATURE:
<223> OTHER INFORMATION: Nucleotide sequence of LacZ-R

<400> SEQUENCE: 2
ttggtgagat gggcgcat                                              18

<210> SEQ ID NO 3
<211> LENGTH: 21
<212> TYPE: DNA
<213> ORGANISM: Artificial
<220> FEATURE:
<223> OTHER INFORMATION: Nucleotide sequence of LacZ-R_177

<400> SEQUENCE: 3
gccttcctgt agccagcttt c                                          21

<210> SEQ ID NO 4
<211> LENGTH: 16
<212> TYPE: DNA
<213> ORGANISM: Artificial
<220> FEATURE:
<223> OTHER INFORMATION: Nucleotide sequence of 16S-F_95

<400> SEQUENCE: 4
agcctgatgc agccat                                                16

<210> SEQ ID NO 5
<211> LENGTH: 23
<212> TYPE: DNA
<213> ORGANISM: Artificial
<220> FEATURE:
<223> OTHER INFORMATION: Nucleotide sequence of 16S-R

<400> SEQUENCE: 5
gagcaaaggt attaacttta ctc                                        23
```

METHOD FOR MODIFYING NUCLEIC ACIDS

TECHNICAL FIELD

The present invention relates to a method for modifying a nucleic acid, which is effective for reducing signals derived from the nucleic acid contained in a sample when a nucleic acid detection method is performed; a kit for use in said method; and a composition therefor.

BACKGROUND ART

Currently, nucleic acid detection technique is a common research means in the field of medicine and biology and has been widely used in qualitative and quantitative measurements. Such nucleic acid detection technique in combination with particularly a nucleic acid amplification method as typified by a PCR method enables detection of the presence of very few cells or microorganisms by targeting a nucleic acid specific to these cells or microorganisms. Therefore, the nucleic acid detection technique has been widely used as a high-sensitivity analysis method for basic research as well as in industry. The nucleic acid detection technique is also utilized for the chasing of distribution channels and authentication by artificially incorporating a nucleic acid of a specific sequence into a material or an article to label it.

On the other hand, a detection method utilizing a nucleic acid amplification method has the problem of interference with analysis of other samples that is caused by amplified nucleic acids produced by nucleic acid amplification reaction during the work of detection. Since the nucleic acid amplification reaction produces an enormous number of molecules of amplified products by the logarithmic nucleic acid amplification, amplified products that are unintentionally present in other samples, reagents, test devices or test environments may be amplified as templates and thereby wrong analysis results may be obtained.

For the purpose of preventing such artificial amplification from amplified products, a means for preventing amplified nucleic acids from interfering with other tests have been developed in addition to general attention to the strict handling of samples, reagents, test devices etc., and the cleaning of test environments. For example, a method of producing an amplified nucleic acid susceptible to uracil-N-glycosylase is known, which method comprises amplifying a nucleic acid in a reaction solution containing deoxyuracil triphosphate. Amplified nucleic acids derived from other tests can be degraded by treating a sample or a reaction solution with uracil-N-glycosylase prior to the amplification reaction. In addition, a method of preventing a nucleic acid from functioning as a template in a nucleic acid amplification reaction is also reported, which method comprises modifying the nucleic acid with a photoactivated psoralen compound via a covalent bond (Non-patent Literature 1).

A technique for modifying a nucleic acid to prevent it from functioning as a template for a nucleic acid amplification reaction has also been used in the detection of microorganisms. It is said that DNA derived from dead cells remains in a sample until several days to three weeks after the cell death. When DNAs are extracted from a sample by a usual procedure, they include DNAs derived from both living cells and dead cells. Thus, for example, when a sample is subjected to a sterilization treatment, the result of sterilization is not fully reflected in a microbial detection method with use of a nucleic acid as an index.

As a solution for the above problem, a method of distinguishing living cells and dead cells which comprises a combination of a nucleic acid-modifying agent with a nucleic acid amplification method has been reported (Non-patent Literature 2, Patent Literature 1). This nucleic acid-based detection method is a method for discriminating living cells from dead cells by using the presence or rate of amplification as an index, which comprises use of a nucleic acid-modifying agent such as ethidium monoazide (EMA) or propidium monoazide (PMA) in combination with a nucleic acid amplification method such as real-time PCR. For example, it is reported that EMA is activated under visible light to be covalently bonded to nucleic acids, so that a nucleic acid amplification reaction is inhibited. At the same time, unbound EMA remaining in a free state in a sample is inactivated by reaction with water molecules. Nucleic acids derived from living cells which EMA has not invaded due to the intact cell walls and cell membranes do not undergo the action of EMA. On the other hand, nucleic acids derived from dead cells which EMA has invaded are modified with the EMA, so that a later nucleic acid amplification reaction is inhibited. Thus, when a sample consisting of a mixture of living cells and dead cells is treated with the above-mentioned nucleic acid-modifying agent, nucleic acids derived from living cells are selectively amplified. To date, such a method has been applied to detection of living cells distinguished from dead cells for many microorganisms such as *Escherichia coli* O157, *Salmonella typhimurium*, *Listeria*, *Campylobacter jejuni*, and *Legionella*. However, it has been reported that a high concentration of a nucleic acid-modifying agent gives damage to living cells, while it ensures the binding to nucleic acid derived from dead cells.

Thus, the modification of nucleic acid has a variety of applications. Therefore, a method for modifying nucleic acids more efficiently is demanded.

CITATION LIST

Patent Literature

Patent Literature 1: JP-B 4127847

Non-Patent Literature

Non-Patent Literature 1: Nucleic Acids Research, Volume 19, Pages 99-107, 1991
Non-Patent Literature 2: Appl. Environ. Microbiol., Volume 73, Pages 8028-8030, 2007

SUMMARY OF INVENTION

Technical Problem

An object of the present invention is to provide a method for efficiently modifying a nucleic acid that is desired to be prevented from being detected, so that the accuracy of various nucleic acid-based detection techniques is improved.

Solution to Problem

The present inventors intensively made efforts to solve the above problem. As a result, they found that nucleic acids could be modified more effectively than when a conventional method was used, by using a method of modifying a nucleic acid contained in a sample which comprises a step of bringing the sample into contact with a nucleic acid-modifying agent in the presence of an acidic polysaccharide and/or a nucleotide, and then completed the present invention.

That is, the present invention generally relates to the following:

[1] A method of modifying a nucleic acid contained in a sample, the method comprising a step of bringing the sample into contact with a nucleic acid-modifying agent in the presence of an acidic polysaccharide and/or a nucleotide;

[2] The method according to [1], wherein the nucleic acid-modifying agent is a compound capable of modifying a nucleic acid by photoactivation;

[3] The method according to [2], wherein the nucleic acid-modifying agent is a compound selected from ethidium monoazide and propidium monoazide;

[4] The method according to [1], wherein the acidic polysaccharide is selected from sodium alginate and chondroitin sulfate B, or the nucleotide is selected from DNA and dNTP;

[5] A method of selectively detecting a nucleic acid derived from a living cell contained in a sample, the method comprising the following steps:
(a) a step of modifying a nucleic acid contained in the sample by the method according to claim 1; and
(b) a step of selectively detecting an unmodified nucleic acid from the sample after the step (a);

[6] The method according to [5], wherein the nucleic acid-modifying agent is a compound capable of modifying a nucleic acid by photoactivation;

[7] The method according to [6], wherein the nucleic acid-modifying agent is a compound selected from ethidium monoazide and propidium monoazide;

[8] The method according to [5], wherein the acidic polysaccharide is selected from sodium alginate and chondroitin sulfate B, or the nucleotide is selected from DNA and dNTP;

[9] The method according to [5], wherein the step (b) is performed by a nucleic acid amplification method;

[10] The method according to [9], wherein the step (b) is performed by real-time PCR;

[11] A kit for modifying a nucleic acid in a sample by the method according to [1], the kit containing:
(a) a nucleic acid-modifying agent; and
(b) an acidic polysaccharide and/or a nucleotide to be used with the nucleic acid-modifying agent of (a);

[12] The kit according to [11], wherein the nucleic acid-modifying agent is a compound capable of modifying a nucleic acid by photoactivation;

[13] The kit according to [12], wherein the nucleic acid-modifying agent is a compound selected from ethidium monoazide and propidium monoazide;

[14] The kit according to [11], wherein the acidic polysaccharide is selected from sodium alginate and chondroitin sulfate B, or the nucleotide is selected from DNA and dNTP;

[15] A kit for selectively detecting a nucleic acid derived from a living cell contained in a sample by the method according to [5], the kit containing:
(a) a nucleic acid-modifying agent;
(b) an acidic polysaccharide and/or a nucleotide to be used with the nucleic acid-modifying agent of (a); and
(c) reagents for nucleic acid detection;

[16] The kit according to [15], wherein the nucleic acid-modifying agent is a compound capable of modifying a nucleic acid by photoactivation;

[17] The kit according to [16], wherein the nucleic acid-modifying agent is a compound selected from ethidium monoazide and propidium monoazide;

[18] The kit according to [15], wherein the acidic polysaccharide is selected from sodium alginate and chondroitin sulfate B, or the nucleotide is selected from DNA and dNTP;

[19] A composition comprising:
(a) a nucleic acid-modifying agent; and
(b) an acidic polysaccharide and/or a nucleotide;

[20] The composition according to [19], wherein the nucleic acid-modifying agent is a compound capable of modifying a nucleic acid by photoactivation;

[21] The composition according to [20], wherein the nucleic acid-modifying agent is a compound selected from ethidium monoazide and propidium monoazide; and

[22] The composition according to [19], wherein the acidic polysaccharide is selected from sodium alginate and chondroitin sulfate B, or the nucleotide is selected from DNA and dNTP.

Effects of Invention

According to the method of the present invention, nucleic acid modification efficiency can be increased in the treatment of bringing a sample into contact with a nucleic acid-modifying agent, and this is extremely useful for increasing the accuracy of food hygiene inspection and clinical testing.

MODE FOR CARRYING OUT INVENTION

The present invention will be described in detail below.
(1) Nucleic Acid Modification Method of the Present Invention The nucleic acid modification method of the present invention is a method of modifying a nucleic acid contained in a sample which comprises a step of bringing the sample into contact with a nucleic acid-modifying agent in the presence of an acidic polysaccharide and/or a nucleotide.

The sample that is a subject for the method of the present invention includes all samples in which nucleic acids can be present. Examples thereof include foods, farm products, marine products, biological tissues and body fluids (e.g., blood, urine, spinal fluid, and pleural effusion), cell culture liquids, chemical products (e.g., pharmaceuticals, agricultural chemicals, and reagents), industrial water, city water, underground water, river water, impounded water, rainwater, drainage, and soil. In particular, the foods include beverages, confectioneries, dairy products, functional foods, and the like. In the present invention, the sample may be the above-mentioned product, biological sample or environmental sample itself, or it may be subjected to pre-treatment such as dissolution, suspension, dilution, concentration or purification. Examples of the pre-treatment include heat treatment, filtration, centrifugation, and the like. The sample may be also subjected to, as a pre-treatment, a treatment for reducing impurities such as proteins and fats present in the sample, for example, an enzymatic treatment with a proteolytic enzyme and a lipolytic enzyme.

The nucleic acid-modifying agent used in the present invention is a substance that can modify a nucleic acid to become an undetectable form by its action. That is, an example of the nucleic acid-modifying agent is a substance that causes any one selected from a change in the ability to hybridize with a complementary strand of a nucleic acid, a change in the function as a template for complementary strand replication, a change of the original sequence, and fragmentation of a nucleic acid, or their plural combinations. Therefore, the nucleic acid modification as used in the present invention includes intercalation of a nucleic acid-modifying agent into a nucleic acid base pair, covalent bonding of a nucleic acid-modifying agent to a nucleic acid, crosslinking of nucleic acids, substitution of a nucleic acid base, and cleavage of a nucleic acid with a nucleic acid-modifying agent. Examples of the nucleic acid-modifying agent suitable for the present invention include EMA (ethidium monoazide), PMA (propidium monoazide), ethidium diazide, psoralen compounds [psoralen, 4'-AMD-MIP (4'-aminomethyl-4,5'-dimethylisopsoralen), AMIP (5-aminomethylisopsoralen), 5-MIP (5-methylisopsoralen), 8-methoxysopsorale, etc.], and propidium iodide. In addition, commercially available reagents, such as, trade names, SYTO Red Fluorescent, BODIPY (4,4-difluor-4-bora-3a, 4a-diaza-s-indacene), YO-PRO-1 dye, Alexa Fluor 488 annexin V, C4-BODIPV500/510CY, and Hoechst 33258 (all are manufactured by Molecular Probes Inc.), can be used. The above-mentioned nucleic acid-modifying agents can be used alone or as a mixture of two or more types. Furthermore, it is also possible to use a modifying agent contained in a commercially available kit such as LIVE/DEAD BacLight Bacterial Viability Kit, ViaGram Red+Bacterial Gram Stain, or Viability Kit (manufactured by Molecular Probes Inc.).

The concentration of the nucleic acid-modifying agent used in the present invention and the duration time of contact of the nucleic acid-modifying agent with a sample can be appropriately selected depending on the sample. For example, the concentration and the duration time can be decided by adding the nucleic acid-modifying agent with different concentrations to a sample, keeping the contact for a certain period of time, and analyzing the modifications of nucleic acids after the reaction. In the case of using EMA, nucleic acid can be modified under the conditions of, for example, the EMA final concentration of 1 to 100 µM and the contact time of 1 minute to 48 hours, preferably at the EMA final concentration of 5 to 70 µM and the contact time of 3 minutes to 10 hours, and more preferably the EMA final concentration of 10 to 50 µM and the contact time of 5 minutes to 5 hours. The step of bringing a sample into contact with a nucleic acid-modifying agent may be performed under conditions suitable for the nucleic acid-modifying agent to be used.

When the nucleic acid-modifying agent that is photoactivatable, such as EMA, PMA or a psoralen compound is used in the method of the present invention, a light irradiation treatment is carried out after contacting the nucleic acid-modifying agent with a sample. In the case of using the nucleic acid-modifying agent that is photoactivatable, the nucleic acid-modifying agent is usually added to a sample to bring the nucleic acid-modifying agent into contact with a nucleic acid under a light-shielding condition at a low temperature (e.g., room temperature to 0° C.) and then subjected to light irradiation, but the present invention is not limited to this case. The wavelength of light used for the light irradiation treatment is not particularly limited as long as it is suitable for the activation of the nucleic acid-modifying agent. For example, a single-wavelength light at a wavelength of 350 to 700 nm or a multi-wavelength light including wavelengths of 350 to 700 nm can be used. The light intensity and irradiation time for the light irradiation treatment can be appropriately selected depending on the nucleic acid-modifying agent, light source, and sample to be used. For example, the light intensity and irradiation time can be determined by analyzing the modifications of nucleic acids after the treatment using varying light intensities and distances between a sample and a light source. In the case of using EMA, it is possible to carry out the light irradiation treatment under the conditions of, for example, using a lamp with 1 to 1000 W, the distance between the lamp and a sample of 1 to 50 cm, and the irradiation time of 1 to 20 minutes. Furthermore, an LED (Light Emitting Diode) lamp with low power consumption and strong light intensity has been developed and can be used in the present invention. In addition, the light irradiation treatment is preferably carried out at a low temperature (e.g., on ice).

The acidic polysaccharide to be used in the method of the present invention includes sulfated polysaccharides containing a sulfate group, represented by fucose sulfate-containing polysaccharide, dextran sulfate, carrageenan, heparin, heparan sulfate, rhamnan sulfate, chondroitin sulfate, chondroitin sulfate B (dermatan sulfate), and the like; polyuronic acids such as hyaluronic acid, alginic acid, and pectin; and salts thereof. Examples of the salts of the above-mentioned acidic polysaccharides include alkali metal salts such as sodium dextran sulfate, sodium alginate, heparin sodium, potassium dextran sulfate, and heparin lithium. The above-mentioned acidic polysaccharides may be naturally occurring substances or chemically or enzymatically synthesized products. In addition, the above-mentioned acidic polysaccharides may be unpurified or partially purified or purified products containing acidic polysaccharides. The above-mentioned acidic polysaccharides may be used alone or as a mixture of two or more types.

The concentration of the acidic polysaccharide to be used in the method of the present invention can be appropriately selected and added depending on the acidic polysaccharide and the sample to be used. For example, the concentration of the acidic polysaccharide can be determined by analyzing the modifications of nucleic acids after the treatment using varying concentrations of the acidic polysaccharide. For example, if sodium alginate is used, its concentration is 1 µg/mL to 100 mg/mL, preferably 10 µg/mL to 10 mg/mL, and more preferably 100 µg/mL to 5 mg/mL. For example, if chondroitin sulfate B is used, its concentration is 10 µg/mL to 1000 mg/mL, preferably 100 µg/mL to 500 mg/mL, and more preferably 1 mg/mL to 100 mg/mL.

If a sample is subjected to the action of a nucleic acid-modifying agent in the presence of the above-mentioned acidic polysaccharide, the proportion of modification of free nucleic acids in the sample is increased, and at the same time, the proportion of modification of non-free nucleic acids, in particular DNAs, in environments that permit contact of the nucleic acid-modifying agent (for example, nucleic acids bound to biomolecules and nucleic acids contained in dead cells having enhanced cell membrane permeability) is also increased. Therefore, it becomes possible to reduce the interference derived from these nucleic acids or DNAs in a nucleic acid detection method. As used herein, the phrase "a sample is subjected to the action of a nucleic acid-modifying agent in the presence of an acidic polysaccharide" means that "an acidic polysaccharide is artificially added to a sample and then the sample is treated with a nucleic acid-modifying agent".

The nucleotide for use in the method of the present invention or the nucleotide used in the present invention means a ribonucleotide or a deoxyribonucleotide constituting a nucleic acid, or a substance comprising its analog as a constituent. Examples of the nucleotide that can be used in the present invention include, but not limited to, DNA, RNA, oligoribonucleotide, oligodeoxyribonucleotide, monoribonucleotide (e.g., monoribonucleoside triphosphate: NTP), and monodeoxyribonucleotide (e.g., monodeoxyribonucleotide triphosphate: dNTP). Inosine nucleotide, deoxyinosine nucleotide, deoxyuridine nucleotide, and triphosphates thereof, which are natural ribonucleotide analogs, and DNA, RNA, oligoribonucleotide and oligodeoxyribonucleotide containing the above-mentioned analogs can also be used in the present invention. NTP includes monoadenosine triphosphate (ATP), monothymidine triphosphate (TTP), monocytidine triphosphate (CTP), monoguanosine triphosphate (GTP), and monouridine triphosphate (UTP). Further, dNTP includes monodeoxyadenosine triphosphate (dATP), monodeoxythymidine triphosphate (dTTP), monodeoxycytidine triphosphate (dCTP), and monodeoxyguanosine triphosphate (dGTP). As used herein, the nucleotide includes salts of the above-mentioned substances (e.g., alkali metal salts). The above-mentioned nucleotides may be natural products or chemically or enzymatically synthesized products. Further, the above-mentioned nucleotides may be unpurified or partially purified or purified products containing nucleotides. The above-mentioned nucleotides can be used alone or as a mixture of two or more types. As one aspect of the present invention, a nucleotide selected from DNA and dNTP can be used. Examples of the DNA used in the present invention include, but not limited to, DNAs derived from easily available animals (calf thymus DNA, salmon sperm DNA, etc.) and DNAs derived from microorganisms (bacterial genomic DNA, bacteriophage DNA, plasmid DNA, etc.). The calf thymus DNA, λ phage DNA (λDNA), and dNTP are commercially available as reagents, and they are suitable for the present invention.

The concentration of the nucleotide to be used in the method of the present invention can be appropriately selected and used depending on the nucleotide and sample to be used. For example, the concentration of the nucleotide can be determined by analyzing the modifications of nucleic acids after the treatment using varying concentrations of the nucleotide. For example, if λDNA is used, its concentration is 10 ng/mL to 10 mg/mL, preferably 100 ng/mL to 1 mg/mL, and more preferably 1 μg/mL to 100 μg/mL. For example, if, deoxy NTP is used, its concentration is 10 μM to 500 mM, preferably 100 μM to 100 mM, and more preferably 1 mM to 50 mM.

If a sample is subjected to the action of a nucleic acid-modifying agent in the presence of the above-mentioned nucleotide, the proportion of modification of free nucleic acids in the sample is increased, and at the same time, the proportion of modification of non-free nucleic acids, in particular DNAs, in environments that permit contact of the nucleic acid-modifying agent (for example, nucleic acids bound to biomolecules and nucleic acids contained in dead cells having enhanced cell membrane permeability) is also increased. Therefore, it becomes possible to reduce the interference derived from these nucleic acids or DNAs in a nucleic acid detection method. As used herein, the phrase "a sample is subjected to the action of a nucleic acid-modifying agent in the presence of a nucleotide" means that "a nucleotide is artificially added to a sample and then the sample is treated with a nucleic acid-modifying agent".

In the method, kit and composition of the present invention, one or more kinds of the above-mentioned acidic polysaccharides and one or more kinds of the above-mentioned nucleotides may be used in combination.

(2) Selective Detection Method of Nucleic Acids Derived from Living Cells According to the Present Invention Cell membrane integrity is important in distinguishing living cells that are able to survive and grow from dead cells that are irreversibly damaged. According to the nucleic acid modification method of the present invention, even a nucleic acid within a cell having enhanced permeability of the cell wall and cell membrane which a nucleic acid-modifying agent can invade can be modified using a nucleic acid-modifying agent having selectivity to a cell membrane. On the other hand, a nucleic acid within a living cell which a nucleic acid-modifying agent cannot invade is not modified. Thus, according to the present invention, a method of selectively detecting a nucleic acid derived from a living cell contained in a sample is provided.

The term "living cell" as used herein refers to a cell that maintains life activity, namely, a cell that maintains metabolic ability and proliferation ability. Further, the living cell has no substantial damage in the structure or form. On the other hand, a dead cell has damage in the cell wall and/or cell membrane and has reduced ability to maintain life activity. The dead cell does not normally grow even under conditions suitable for the growth of the cell. Such a dead cell is in a state where an extracellular substance may invade the dead cell.

When the nucleic acid modification method of the present invention is applied to a sample in which cells may be present, only nucleic acids in living cells are not affected by the action of a nucleic acid-modifying agent and they keep a state capable of being detected by a nucleic acid detection method, for example, a nucleic acid amplification method. Accordingly, use of the method of the present invention makes it possible to specifically detect the presence of living cells, for example, microbial living cells, regardless of the presence of dead cells.

The cell that is a subject for the method of the present invention may be a eukaryotic cell or prokaryotic cell, and examples thereof include microorganisms such as yeasts, fungi and bacteria, animal cells, and plant cells. The bacteria include both Gram-positive and Gram-negative bacteria. Examples of the Gram-positive bacteria include *Bacillus* bacteria (*B. cereus, B. anthracia*, etc.), *Staphylococcus* bacteria (*S. aureus, S. epidermidis*, etc.), *Listeria* bacteria (*L. monocytogenes*, etc.), *Clostridium* bacteria (*C. botulinum, C. perfringens*, etc.), *Streptococcus* bacteria (*S. pneumoniae*, etc.), *Mycobacterium* bacteria, and the like. Examples of the Gram-negative bacteria include *Escherichia* bacteria (*E. coli*, etc.), *Salmonella* bacteria (*S. enteritidis, S. typhimurium*, etc.), *Vibrio* bacteria (*V. parahaemolyticus*, etc.), *Cronobacter* bacteria (formerly *E. sakazaki*, etc.), *Legionella* bacteria (*L. pneumophila*, etc.), *Pseudomonas* bacteria, and the like.

The method of the present invention can be carried out using various samples as the subject, as described above. However, from the viewpoint of maintaining the selectivity, it is necessary to avoid a treatment of the sample that leads to damage to the cell membrane.

A method of detecting a nucleic acid derived from a living cell contained in a sample of the present invention is carried out by the following steps of (a) and (b):

(a) a step of modifying a nucleic acid contained in the sample by the nucleic acid modification method of the present invention; and (b) a step of selectively detecting an unmodified nucleic acid from the sample after the step (a).

The step (a) in the method of the present invention is a step of performing the modification of a nucleic acid in a sample by bringing the sample into contact with a nucleic acid-modifying agent in the presence of an acidic polysaccharide and/or a nucleotide, as described in the above (1). For example, a nucleic acid can be modified by adding a nucleic acid-modifying agent and an acidic polysaccharide and/or a nucleotide to a sample and placing the sample under appropriate conditions. In the method of the present invention, when using a nucleic acid-modifying agent that is photoactivatable as described in the above (1), a light irradiation treatment can be carried out simultaneously with or after the step (a). In addition, the step (a) and the light irradiation treatment may be repeated several times, for example, two to five times. That is, it is possible to repeatedly perform the addition of the nucleic acid-modifying agent and the light irradiation treatment. In the case of repeating the step (a) and the light irradiation treatment, an appropriate medium for the growth of living cells contained in a sample can be added to the sample after the light irradiation treatment, as described in WO 2009/022558, and thereby a step of culturing the living cells can be combined.

Further, after the step (a), a step of removing the nucleic acid-modifying agent can be carried out. As a method of removing the nucleic acid-modifying agent, a solid-liquid separation method known in the art can be used. An example of such a method comprises centrifuging a sample to separate a precipitate containing cells and a supernatant containing the nucleic acid-modifying agent and then removing the supernatant. In this case, after removing the nucleic acid-modifying agent, a step of washing the cells can be also added.

In addition, after the step (a), a step of lysing living cells and/or a step of extracting a nucleic acid can be carried out. Examples of a method of cell lysis and a method of nucleic acid extraction include various methods such as a proteinase K/phenol extraction method, a proteinase K/phenol/chloroform extraction method, an alkaline lysis method, an alkali-SDS method, and a lysing enzyme method, in addition to cell destruction by heat treatment (heat extraction). Among these methods, a suitable cell lysis method and/or a suitable nucleic acid extraction method may be selected depending on the nucleic acid detection method that is carried out in the step (b) mentioned later.

In the step (b) of the method of the present invention, a nucleic acid of a living cell can be specifically detected by selectively detecting an unmodified nucleic acid from the sample after the step (a). That is, it becomes possible to reduce the noise caused by the nucleic acids of dead cells in the detection of living cells based on nucleic acids, which makes it possible to accurately detect the presence of living cells in the sample with high sensitivity.

In the step (b), a method of selectively detecting an unmodified nucleic acid can be appropriately selected depending on the nucleic acid modification method of the step (a). For example, if as a result of selective modification of dead cell DNA (as well as free DNA), the nucleic acid amplification reaction using the DNA as a template is inhibited, a nucleic acid amplification method (DNA amplification method) can be selected as the method for detecting nucleic acids. The DNA amplification method includes a PCR method, an ICAN method, a LAMP method, a SDA method, a LCR method, an RCA method, and a SMAP method. An unmodified nucleic acid can be selectively detected by subjecting a reaction solution after nucleic acid amplification reaction to a conventional analysis method such as gel electrophoresis, so that the amount and the base length of the amplified nucleic acid are analyzed. Further, a method of detecting and quantifying a nucleic acid in real time can be also used, and example thereof include an intercalator method, a TaqMan method, a Scorpion method, a cycling probe method, and a hybridization probe method. These nucleic acid amplification methods and real-time detection methods are described in many reviews, and a person skilled in the art is able to make a selection from many commercially available kits.

In the nucleic acid amplification method or in the real-time detection method, a target region of a nucleic acid to be detected can be appropriately selected depending on the cell to be detected. The target region may be selected from the genome sequences of chromosomes of the cell, or from the sequences of episomes such as a mitochondrial genome, a chloroplast genome, or a plasmid. Further, when different types of cells from the cells to be detected are contained in the sample, it is preferred to select a sequence specific to the cell to be detected as the target region. A sequence common to two or more species of cells may also be selected as the target region. In addition, the target region may be one area or may be a plurality of areas. It is also possible to set a target region specific to the cell to be detected and a target region which a wide range of cells have. The length of the target region is 40 to 5000 bases in length, preferably 60 to 1000 bases in length, and particularly preferably 70 to 200 bases in length.

Primers or probes to be used in the nucleic acid amplification method or in the real-time detection method can be designed based on the target region as described above depending on the nucleic acid amplification method or the real-time detection method.

It is possible to detect a microorganism surviving in a sample by performing the method of the present invention while targeting the microorganism. In the nucleic acid amplification method, a target gene/nucleic acid region is not particularly limited and may be appropriately selected in consideration of specificity and detection sensitivity. If the microorganism to be detected is a pathogenic bacterium, it is possible to select a target region from the pathogenic gene so as to distinguish the pathogenic bacterium from non-pathogenic microorganisms belonging to the same species or genus. Examples of the pathogenic gene include verotoxin type-1 or type-2 gene derived from *E. coli* O-157, heat-stable enterotoxin gene (STh) or heat-labile enterotoxin gene (STp) derived from toxigenic *E. coli*, invasive factor-related gene (invA) derived from *Salmonella* bacteria, heat-resistant hemolysin gene (tdh) derived from *Vibrio parahaemolyticus*, cereulide gene (CRS) derived from *Bacillus cereus*, internalin A gene (intA) derived from *Listeria* bacteria, outer membrane protein A gene (ompA) derived from *Enterobacter sakazakii*, cytolethal distending toxin (cdt) gene derived from *Campylobacter*, and the like. In addition, a gene encoding ribosomal RNA (16SrRNA, 23SrRNA) widely used for the microbe detection or its spacer region can be used as a target.

Further, an analysis method in the case of employing a real-time PCR method as a detection method in the step (b) is exemplified below. In the real-time PCR method, changes in a fluorescent signal are monitored. The fluorescent signal intensity increases when a PCR amplified product is provided, and an amplification curve is drawn. In general, changes in the fluorescence intensity of up to about 1 to 10 amplification cycles of PCR are a noise level equal to zero and considered as a sample blank (baseline). When compared with the sample blank, a fluorescent signal intensity wherein a significant difference in the fluorescent signal is observed is set as a threshold value. A cycle threshold value (Ct value) is defined as the number of PCR cycles exceeding the threshold value in the amplification curve. Thus, when the initial amount of DNA template in a PCR reaction solution is larger, the Ct value is smaller, and when the initial amount of template DNA is smaller, the Ct value is larger.

Further, as the proportion of the occurrence of modification of nucleic acids in the target region is increased, the Ct value is a larger value even if the total amount of nucleic acids is the same. In addition, it is possible to confirm whether or not an amplified product is derived from the target region by a melting curve analysis (Tm analysis) to analyze the melting temperature of the amplified product.

(3) Kit and Composition of the Present Invention

The kit of the present invention is a kit for modifying a nucleic acid in a sample by the method of the present invention as described in the above (1), the kit containing:
  (a) a nucleic acid-modifying agent; and
  (b) an acidic polysaccharide and/or a nucleotide to be used with the nucleic acid-modifying agent of (a).

In addition, another kit of the present invention includes a kit for selectively detecting a nucleic acid derived from a living cell contained in a sample by the method of the present invention as described in the above (2), said kit containing:
  (a) a nucleic acid-modifying agent;
  (b) an acidic polysaccharide and/or a nucleotide to be used with the nucleic acid-modifying agent of (a); and
  (c) reagents for nucleic acid detection.

The nucleic acid-modifying agent, acidic polysaccharide, and nucleotide contained in the kit of the present invention are as described in the above (1). The reagents for nucleic acid detection contained in the kit of the present invention are reagents used in the nucleic acid detection method as described in the above (2). For example, when employing a PCR method as the nucleic acid detection method, the reagents for nucleic acid detection include a reaction buffer, a primer pair to amplify a target region, a DNA polymerase, nucleosides, a magnesium salt, and the like. Furthermore, the reagents for nucleic acid detection include an intercalator dye [SYBR (registered trademark) Green I, etc.], a detection probe, and an enzyme (e.g., RNase H, etc.) necessary for a detection reaction, depending on a nucleic acid detection method.

The kit of the present invention may further contain a reagent for diluting a sample or a nucleic acid-modifying agent, a buffer for a nucleic acid-modification reaction, instructions describing the method of the present invention, a reagent for removing and cleaning contaminants from a sample, a positive control, a negative control, and the like.

The composition of the present invention is used in the nucleic acid modification method of the present invention as described in the above (1) or in the method of selectively detecting a nucleic acid derived from a living cell of the present invention as described in the above (2), and contains (a) a nucleic acid-modifying agent and (b) an acidic polysaccharide and/or a nucleotide. The nucleic acid-modifying agent, acidic polysaccharide, and nucleotide contained in the composition of the present invention are as described in the above (1).

As explained above in detail, the present invention provides a method of enhancing the action of a nucleic acid-modifying agent by an enhancer comprising an acidic polysaccharide and/or a nucleotide as an active ingredient(s), as well as provides an enhancer for a nucleic acid-modifying agent, which comprises an acidic polysaccharide and/or a nucleotide as an active ingredient(s). The method and the enhancer are useful for the modification of a nucleic acid of interest in a sample and can be applied to various industrial fields.

EXAMPLES

Then, the present invention will be described in more detail by way of Examples, but the present invention is not intended to be limited to the following Examples.

Example 1

Effect of Acidic Polysaccharide

Using a genomic DNA sample of *E. coli* to which an acidic polysaccharide (sodium alginate or chondroitin sulfate B) had been added, an EMA treatment was performed once and detection sensitivities were compared by a real-time PCR method for a LacZ gene as a target region.

(1) Preparation of Sample

Genomic DNA prepared from *E. coli* K-12 was adjusted to $1 \times 10^8$ copies/30 μL in TE buffer [10 mM Tris-HCl (pH 8.0)/0.1 mM EDTA] to obtain a specimen solution. In addition, as an acidic polysaccharide, 100 μg or 10 μg of sodium aliginate (Sodium Alginate 80-120 cp, manufactured by Wako Pure Chemical Industries, catalog number: 194-13321, hereinafter also referred to as "AlgNa") or 480 μg of chondroitin sulfate B (dermatan sulfate, manufactured by Sigma, catalog number: C3788) was added to the specimen solution. A specimen solution to which an acidic polysaccharide had not been added was prepared as a control. Then all the specimen solutions were adjusted to 50 μL with sterile water. Herein, the number of copies refers to the number of copies calculated from the weight of a nucleic acid.

(2) EMA Treatment

EMA (ethidium bromide monoazide, manufactured by Sigma-Aldrich Corporation: catalog number: E2028) was completely dissolved to 5 mM in DMSO, and stored at −20° C. When used, this EMA solution was thawed and diluted with sterile water to 300 μM. The aqueous EMA solution (5 μL each) was added to 50 μL of each of the specimen solutions of the genomic DNA. The specimen solutions were allowed to stand at 4° C. for 15 minutes under a light-shielding condition. Then, each specimen solution was placed on ice and irradiated for 5 minutes by using a photographic lighting lamp of 500 W (PRS 500 W: 100 V, 500 W, manufactured by Iwasaki Electric Co., Ltd.) placed at a distance of 20 cm from the specimen solution (The process from the addition of EMA solution to the light irradiation is sometimes referred to as "EMA treatment").

Further, a specimen solution which was prepared as described in (1) except that the EMA treatment was not performed was prepared. The specimen solutions with EMA treatment and the specimen solutions without EMA treatment were diluted to 100 μL with sterile water.

(3) PCR Targeting a Region of LacZ Gene (Amplification Chain Length: 70 bp)

A PCR reaction solution (total volume 20 μL) with the following composition was prepared.
  SYBR Premix Ex Taq (manufactured by Takara Bio Inc., catalog number: RR041A): 10 μL
  4 pmol/μL, LazZ-F DNA (Sequence ID NO 1): 1 μL
  4 pmol/μL, LacZ-R DNA (Sequence ID NO 2): 1 μL
  Sterile water: 7 μL
  Template DNA (the diluted specimen solution): 1 μL Each specimen solution (1 μL) prepared in Example 1-(2) was used as a template DNA. In other words, 20 μL of the reaction solution contains $10^6$ copies of *E. coli* genome as a template DNA. As a control, a reaction solution containing 1 μL of sterilized water instead of the diluted specimen solution was prepared. In order to amplify the LacZ gene of the target region, the reaction solution was subjected to PCR under the conditions of holding at 95° C. for 30 seconds and then performing the reaction of 40 cycles in which one cycle consisted of at 95° C. for 5 seconds and at 60° C. for 30 seconds. In the reaction, a real-time PCR instrument, Thermal Cycler Dice Real Time System (manufactured by Takara Bio Inc., model number: TP800) or Thermal Cycler Dice Real Time System II (manufactured by Takara Bio Inc., model number: TP900) was used, and the number of cycles exceeding a threshold value on a PCR amplification curve (hereinafter referred to as the "Ct value") was measured. In addition, after the PCR, melting curve analysis (Tm analysis) of the amplified product was performed under the condition of raising the temperature from 60° C. to 95° C.

(4) Test Results

The Ct values and Tm analytical values obtained by the PCR in Example 1-(3) are shown in Table 1.

TABLE 1

| Acidic polysaccharide | Copy number | Without EMA treatment Ct value | Without EMA treatment Tm value | With EMA treatment Ct value | With EMA treatment Tm value |
|---|---|---|---|---|---|
| None | $10^6$ | 18.41 | 83.48 | 28.83 | 83.36 |
|  |  | 18.38 | 83.39 | 28.62 | 83.21 |
|  |  | 18.34 | 83.47 | 28.72 | 83.33 |
|  |  | 18.57 | 83.53 | 28.67 | 83.32 |
| AlgNa 10 µg | $10^6$ | 18.50 | 83.46 | 29.81 | 83.27 |
|  |  | 18.44 | 83.43 | 29.30 | 83.21 |
|  |  | 18.43 | 83.42 | 29.37 | 83.37 |
|  |  | 18.42 | 83.35 | 29.66 | 83.36 |
| AlgNa 100 µg | $10^6$ | 18.44 | 83.45 | 33.76 | 83.27 |
|  |  | 18.21 | 83.41 | 33.46 | 83.30 |
|  |  | 18.12 | 83.34 | 33.28 | 83.13 |
|  |  | 18.29 | 83.49 | 32.45 | 83.41 |
| Chondroitin sulfate 480 µg | $10^6$ | 18.72 | 83.61 | 31.58 | 83.36 |
|  |  | 18.46 | 83.54 | 31.98 | 83.38 |

As seen from Table 1, since there was no change in the Ct values of the specimen solutions without EMA treatment, it could be confirmed that PCR was not inhibited by the addition of an acidic polysaccharide. When the results of the group with EMA treatment were compared, the Ct value of the specimen solution to which an acidic polysaccharide was added was slower by about 1 to 5 than that of the group without the addition of an acidic polysaccharide. Thus, the addition of an acidic polysaccharide probably promoted the DNA modification with EMA, resulting in reduction of PCR efficiency. In addition, Tm analytical values of the amplified products were all in the range of 83.4±0.5, and it was confirmed that any non-specific amplification did not occur.

Example 2

Effect of Acidic Polysaccharides in Three Times Treatment with EMA (1) Preparation of Sample Genomic DNA prepared from *E. coli* JM109 was subjected to a 10 times serial dilution with TE buffer to prepare DNA solutions containing the genome at $1\times10^8$ to $1\times10^3$ copies/30 µL. Except for this, in the same manner as in Example 1-(1), specimen solutions of *E. coli* genomic DNA were prepared.

(2) EMA Treatment

The specimen solution of *E. coli* genomic DNA prepared in Example 2-(1) was subjected to an EMA treatment in the same manner as in Example 1-(2). After the treatment, further 5 µL of an aqueous EMA solution was added to the specimen solution, and an EMA treatment with visible light irradiation was repeated twice. In total, three EMA treatments were performed. Therefore, after the three EMA treatments, the volume of the specimen solution was 65 µL.

The specimen solutions that were treated with EMA and specimen solutions that were not treated with EMA as controls were prepared and adjusted to 100 µL with sterile water.

(3) PCR Targeting a Region of LacZ Gene

Using the dilution (1 µL) of each specimen solution prepared in Example 2-(2) as a template DNA, PCR targeting a region of the LacZ gene was performed in the same manner as in Example 1-(3). 20 µL of the reaction solution contains $10^6$ to 10 copies of *E. coli* genome as the template DNA.

(4) Test Results

The Ct values and Tm analytical values obtained by PCR in Example 2-(3) are shown in Table 2. Herein, the symbol "-" in the Table indicates that the amplification of the LacZ gene by PCR was not detected.

TABLE 2

| | No addition of AlgNa | | | | Addition of AlgNa | | | |
|---|---|---|---|---|---|---|---|---|
| | Without EMA treatment | | With EMA treatment | | Without EMA treatment | | With EMA treatment | |
| Copy number of genomic DNA | Ct value | Tm value | Ct value | Tm value | Ct value | Tm value | Ct value | Tm value |
| 10 | 31.91 | 83.21 | — | — | 32.11 | 83.29 | — | — |
|  | 32.44 | 83.24 | — | — | 31.99 | 83.23 | — | — |
| $10^2$ | 28.81 | 83.29 | 38.48 | 83.15 | 29.06 | 83.31 | — | — |
|  | 29.00 | 83.29 | — | — | 29.03 | 83.32 | — | — |
| $10^3$ | 25.59 | 83.38 | 35.35 | 83.27 | 25.52 | 83.38 | — | — |
|  | 25.57 | 83.36 | 35.02 | 83.23 | 25.63 | 83.41 | — | — |
| $10^4$ | 22.12 | 83.37 | 29.86 | 83.43 | 22.25 | 83.42 | — | — |
|  | 22.37 | 83.40 | 29.84 | 83.33 | 22.45 | 83.40 | — | — |
| $10^5$ | 19.01 | 83.27 | 28.54 | 83.40 | 19.09 | 83.41 | — | — |
|  | 18.88 | 83.37 | 28.43 | 83.39 | 19.17 | 83.33 | — | — |
| $10^6$ | 15.66 | 83.36 | 33.49 | 83.22 | 15.93 | 83.40 | 30.28 | 83.34 |
|  | 15.75 | 83.35 | 34.14 | 83.18 | 16.16 | 83.35 | 31.24 | 83.28 |

As seen from Table 2, when the results of the group with EMA treatment were compared, the LacZ gene was detected in the reaction solution containing a specimen solution to which an acidic polysaccharide was not added and which contained $10^6$ to $10^3$ copies of genome, whereas the amplification of the LacZ gene was not detected in the reaction solution containing a specimen solution to which an acidic polysaccharide was added and which contained $10^5$ to 10 copies of genome. Thus, the addition of an acidic polysaccharide probably promoted the DNA modification with EMA, resulting in reduction of PCR efficiency. In addition, Tm analytical values of the amplified products were 83.4±0.5, indicating that there was no difference in the specimen solutions of each group.

Example 3

Effect of Acidic Polysaccharides in Distinguishing Between Living Cells and Dead Cells of *E. coli*

(1) Preparation of Sample

Fifty µL of *E. coli* JM109 competent cells (manufactured by Takara Bio Inc., Catalog No.: 9052) were inoculated into 5 mL of an LB liquid medium, and cultured with shaking at about 130 rpm in a constant temperature bath at 37° C. for 13 to 16 hours, thereby to obtain a suspension of living cells. Further, about 700 μL of the suspension of living cells was placed in a 1.5 mL microtube and warmed with a heat block at 100° C. for 5 minutes to prepare a suspension of dead cells.

The prepared suspension of *E. coli* living cells was serially diluted 10-fold with a fresh LB liquid medium to prepare 1 to $10^6$-fold diluted suspensions of living cells. The suspension of the dead cells was diluted $10^2$-fold. To 20 μL of each diluted suspension of living cells was added 10 μL of the $10^2$-fold diluted suspension of dead cells. To a mixed suspension of living cells and dead cells thus prepared, 100 μg of sodium alginate was added, and adjusted to 50 μL with sterile water to prepare a specimen solution. Also, the mixed suspension of living cells and dead cells was adjusted to 50 μL with sterile water without addition of sodium alginate to prepare a specimen solution.

(2) EMA Treatment and DNA Extraction Process

Each specimen solution prepared in Example 3-(1) was subjected to three EMA treatments in the same manner as in Example 2-(2). Therefore, after the three EMA treatments, the volume of the specimen solution was 65 μL. The specimen solutions that were treated with EMA and specimen solutions that were not treated with EMA as controls were adjusted to 100 μL with sterile water, and warmed with a heat block at 100° C. for 5 minutes to thermally extract DNA.

(3) PCR Targeting a Region of LacZ Gene

Each thermal extract prepared in Example 3-(2) was centrifuged at 15,000 rpm for 2 minutes. Using the supernatant thus obtained (1 μL) as a template DNA, PCR targeting a region of the LacZ gene was performed in the same manner as in Example 1-(3).

(4) Test Results

For the Ct values and Tm analytical values obtained by PCR in Example 3-(3), the results of specimen solutions treated with EMA are shown in Table 3, and the results of *E. coli* specimen solutions not treated with EMA are shown in Table 4. Further, equations showing a standard curve calculated from the Ct values and correlation coefficients (R2) are shown in Table 5. Herein, the symbol "-" in the Tables indicates that the amplification of the LacZ gene by PCR was not detected. In addition, AlgNa in Table 5 represents sodium alginate.

TABLE 3

| | EMA treatment | | | |
|---|---|---|---|---|
| | Living cells + Dead cells | | Living cells + Dead cells + AlgNa | |
| Dilution (-fold) | Ct value | Tm value | Ct value | Tm value |
| $10^6$ | 38.25 | 83.55 | — | — |
| | 35.49 | 83.36 | 35.82 | 83.46 |
| $10^5$ | 36.92 | 83.21 | 34.61 | 83.30 |
| | 34.98 | 83.23 | 34.55 | 83.31 |
| $10^4$ | 34.92 | 83.32 | 32.98 | 83.41 |
| | 33.89 | 83.28 | 33.04 | 83.42 |
| $10^3$ | 30.55 | 83.52 | 30.08 | 83.47 |
| | 30.68 | 83.46 | 30.25 | 83.45 |
| $10^2$ | 27.03 | 83.60 | 26.93 | 83.52 |
| | 26.80 | 83.52 | 27.07 | 83.45 |
| 10 | 23.25 | 83.58 | 22.93 | 83.51 |
| | 23.23 | 83.46 | 23.17 | 83.49 |
| 1 | 20.20 | 83.50 | 19.92 | 83.47 |
| | 20.09 | 83.45 | 19.95 | 83.44 |

TABLE 4

| No EMA treatment | Living cells | | Living cells + Dead cells | | Living cells + Dead cells + AlgNa | |
|---|---|---|---|---|---|---|
| Dilution (-fold) | Ct value | Tm value | Ct value | Tm value | Ct value | Tm value |
| $10^6$ | — | — | 25.38 | 83.58 | 25.68 | 83.50 |
| | 36.60 | 83.57 | 25.22 | 83.61 | 25.21 | 83.59 |
| $10^5$ | 35.87 | 83.25 | 25.56 | 83.50 | 25.35 | 83.46 |
| | 34.72 | 83.32 | 25.40 | 83.55 | 25.31 | 83.45 |
| $10^4$ | 32.02 | 83.39 | 25.14 | 83.52 | 25.48 | 83.48 |
| | 31.81 | 83.46 | 25.22 | 83.57 | 25.50 | 83.48 |
| $10^3$ | 28.41 | 83.52 | 25.03 | 83.50 | 25.29 | 83.48 |
| | 28.28 | 83.57 | 25.06 | 83.56 | 25.20 | 83.50 |
| $10^2$ | 25.30 | 83.53 | 24.57 | 83.51 | 24.59 | 83.45 |
| | 25.22 | 83.45 | 24.51 | 83.55 | 24.62 | 83.52 |
| 10 | 21.73 | 83.44 | 22.28 | 83.48 | 22.01 | 83.41 |
| | 21.55 | 83.49 | 22.41 | 83.49 | 21.95 | 83.38 |
| 1 | 18.74 | 83.43 | 19.53 | 83.42 | 19.09 | 83.40 |
| | 18.77 | 83.47 | 19.57 | 83.49 | 18.85 | 83.47 |

TABLE 5

| | Condition | R2 | Standard curve |
|---|---|---|---|
| EMA treatment | Living cells + Dead cells | 0.958 | Y = -2.967*LOG(X) + 20.83 |
| | Living cells + Dead cells + AlgNa | 0.974 | Y = -2.844*LOG(X) + 20.69 |
| No EMA treatment | Living cells | 0.992 | Y = -3.196*LOG(X) + 18.76 |
| | Living cells + Dead cells | 0.714 | Y = -0.862*LOG(X) + 21.33 |
| | Living cells + Dead cells + AlgNa | 0.698 | Y = -0.964*LOG(X) + 20.98 |

As seen from Table 4, when a certain amount of a suspension of dead cells was added to the specimen solutions that were not treated with EMA and that were diluted with dilution rates higher than $10^3$ times, almost the same Ct values were obtained regardless of the presence or absence of sodium alginate, indicating that the addition of sodium alginate did not vary the Ct value. As seen from Table 3, in the specimen solutions treated with EMA, the Ct values reflected the amount of living cells regardless of the addition of a suspension of dead cells. Thus, the EMA treatment probably suppressed the amplification of dead cell DNA as a template. In addition, as seen from the numerical values of R2 in Table 5, the correlation coefficient was improved by the addition of an acidic polysaccharide in the treatment with EMA, and it was found that a low amount of template could be quantitatively detected. Moreover, the Tm analytical values of the amplified products were all in the range of 83.4±0.5, and it was confirmed that any non-specific amplification did not occur in this study.

Example 4

Effect of Nucleotides

Using an *E. coli* genomic DNA sample to which λDNA was added as a nucleotide, an EMA treatment was performed three times, and detection sensitivities were compared by a real-time PCR method targeting the LacZ gene.

(1) Preparation of Sample

Genomic DNA prepared from *E. coli* K-12 was serially 10-fold diluted with TE buffer [10 mM Tris-HCl (pH 8.0)/ 0.1 mM EDTA] and adjusted to $5\times10^7$ copies/20 μL to $5\times10$ copies/20 μL to obtain a specimen solution. In addition, 250 ng of λDNA (manufactured by Takara Bio Inc., Catalog Number: 3010) as a nucleotide was added to the specimen solution. A specimen solution to which a nucleotide was not added was prepared as a control. Then all the specimen solutions were adjusted to 30 μL with sterile water. Herein, the number of copies refers to the number of copies calculated from the weight of genomic DNA.

(2) EMA Treatment

EMA (3 μL each) was added to 30 μL of each specimen solution of the genomic DNA, and in total three EMA treatments were performed, in the same manner as in Example 2-(2). Therefore, after the three EMA treatments, the volume of the specimen solution was 39 μL.

Further, a specimen solution which was prepared as described in Example 4-(1) except that the EMA treatment was not performed was prepared. The specimen solutions with EMA treatment and the specimen solutions without EMA treatment were diluted to 50 μL with sterile water.

(3) PCR Targeting LacZ Gene

A PCR reaction solution (total volume 20 μL) with the following composition was prepared.

SYBR Premix Ex Taq (manufactured by Takara Bio Inc., catalog number: RR041A): 10 μL
4 pmol/μL, LazZ-F DNA (Sequence ID NO 1): 1 μL
4 pmol/μL, LacZ-R DNA (Sequence ID NO 2): 1 μL
Sterile water: 7 μL
Template DNA (the diluted specimen solution): 1 μL Each specimen solution (1 μL) prepared in Example 4-(2) was used as a template DNA. In other words, 20 μL of the reaction solution contains $10^6$ copies to 1 copy of the template DNA. As a control, a reaction solution containing 1 μL of sterile water instead of the diluted specimen solution was prepared. In order to amplify the target LacZ gene, the reaction solution was subjected to PCR under the conditions of holding at 95° C. for 30 seconds and then performing the reaction of 40 cycles in which one cycle consisted of at 95° C. for 5 seconds and at 60° C. for 30 seconds. In the reaction, a real-time PCR instrument, Thermal Cycler Dice Real Time System (manufactured by Takara Bio Inc., model number: TP800) or Thermal Cycler Dice Real Time System II (manufactured by Takara Bio Inc., model number: TP900) was used. A Ct value was calculated based on a PCR amplification curve. The quantified number of copies was calculated based on a calibration curve (hereinafter referred to as "Qty value"). In addition, after the PCR, melting curve analysis (Tm analysis) of the amplified product was performed under the condition of raising the temperature from 60° C. to 95° C.

(4) Test Results

The Ct values and Tm analytical values obtained by PCR in Example 4-(3) are shown in Table 6. Herein, the symbol "-" in the Table indicates that the amplification of the LacZ gene by PCR was not detected.

TABLE 6

| | No addition of nucleotide | | | | | Addition of nucleotide | | | | |
|---|---|---|---|---|---|---|---|---|---|---|
| | 1. No EMA treatment | | 2. EMA treatment | | | 3. No EMA treatment | | 4. EMA treatment | | |
| Copy number | Ct value | Tm value | Ct value | Qty value | Tm value | Ct value | Tm#1 | Ct value | Qty value | Tm value |
| 1 | — | — | — | — | — | — | — | — | — | — |
|  | — | — | — | — | — | — | — | — | — | — |
| 10 | 35.83 | 83.53 | — | — | — | 33.96 | 83.76 | — | — | — |
|  | 34.72 | 83.46 | — | — | — | 34.62 | 83.84 | — | — | — |
| $10^2$ | 31.90 | 83.53 | — | — | — | 31.68 | 83.78 | — | — | — |
|  | 31.56 | 83.61 | — | — | — | 31.74 | 83.73 | — | — | — |
| $10^3$ | 28.11 | 83.61 | 37.11 | 2.61 | 83.76 | 28.39 | 83.87 | — | — | — |
|  | 28.48 | 83.70 | 39.19 | 0.628 | 83.72 | 28.58 | 83.95 | — | — | — |
| $10^4$ | 24.99 | 83.55 | 32.83 | 48.8 | 83.70 | 25.18 | 83.79 | — | — | — |
|  | 25.03 | 83.64 | 32.47 | 62.4 | 83.65 | 25.19 | 83.87 | — | — | — |
| $10^5$ | 21.69 | 83.41 | 29.61 | 441 | 83.63 | 21.86 | 83.71 | — | — | — |
|  | 21.64 | 83.51 | 29.75 | 401 | 83.54 | 21.81 | 83.75 | 36.74 | 2.21 | 83.30 |
| $10^6$ | 18.45 | 83.36 | 32.04 | 83.7 | 83.49 | 18.50 | 83.69 | 37.15 | 1.65 | 83.31 |
|  | 18.39 | 83.48 | 31.80 | 98.6 | 83.40 | 18.60 | 83.73 | 36.92 | 1.94 | 83.21 |

As seen from Table 6, when the Qty values in the case of 2 and 4 wherein the EMA treatment was performed were compared, several tens to several hundreds of copies of the genomic DNA was detected from the reaction solution containing $10^6$ to $10^4$ copies of the genomic DNA in the case 2 with no addition of nucleotide, whereas in the case 4 with the addition of nucleotide, a few copies or less of the genomic DNA was detected, which was almost equivalent to detection limit or less. Thus, the addition of a nucleotide probably promoted the DNA modification with EMA, resulting in reduction of the PCR efficiency. In addition, the Tm analytical values of the amplified products were 83.6±0.5, indicating that there was no difference among the specimen solutions and the respective groups.

Example 5

Effect of Nucleotides in Distinguishing Between Living Cells and Dead Cells of *E. coli*

(1) Preparation of Sample

Fifty μL of *E. coli* JM109 competent cells (manufactured by Takara Bio Inc., Catalog No.: 9052) were inoculated into 5 mL of an LB liquid medium, and cultured with shaking at about 130 rpm in a constant temperature bath at 37° C. for 13 to 16 hours, thereby to obtain a suspension of living cells. Further, about 700 μL of the suspension of living cells was placed in a 1.5 mL microtube and warmed with a heat block at 100° C. for 5 minutes to prepare a suspension of dead cells.

The prepared suspension of *E. coli* living cells was serially diluted 10-fold with a fresh LB liquid medium to prepare 1 to $10^6$-fold diluted suspensions of living cells. The suspension of the dead cells was diluted $10^2$-fold. To 15 μL of each diluted suspension of living cells was added 10 μL of the $10^2$-fold diluted suspension of dead cells. To a mixed suspension of living cells and dead cells thus prepared, 250 μg of λDNA as a nucleotide was added, and adjusted to 30 μL with sterile water to prepare a specimen solution. Also, the mixed suspension of living cells and dead cells was adjusted to 30 µL with sterile water without addition of λDNA to prepare a specimen solution.

(2) EMA Treatment and DNA Extraction Process

Each specimen solution prepared in Example 5-(1) was subjected to three EMA treatments in the same manner as in Example 4-(2). Therefore, after the three EMA treatments, the volume of the specimen solution was 39 µL. The specimen solutions that were treated with EMA and specimen solutions that were not treated with EMA as controls were adjusted to 50 µL with sterile water, and warmed with a heat block at 100° C. for 5 minutes to thermally extract DNA.

(3) PCR Targeting LacZ Gene

Each thermal extract prepared in Example 5-(2) was centrifuged at 15,000 rpm for 2 minutes, and using 1 µL of the supernatant as a template DNA, PCR targeting the LacZ gene was performed in the same manner as in Example 4-(3).

(4) Test Results

The results of the Ct values and Tm analytical values obtained by PCR in Example 5-(3) are shown in Table 7. Further, equations showing a standard curve calculated from the Ct values and correlation coefficients (R2) are shown in Table 8. Herein, the symbol "-" in the Tables indicates that the amplification of the LacZ gene by PCR was not detected.

TABLE 7

| Dilution (–fold) | EMA treatment | | | | | | No EMA treatment | |
|---|---|---|---|---|---|---|---|---|
| | Living cells + λDNA | | Living cells + Dead cells + λDNA | | Living cells + Dead cells | | Living cells + Dead cells + λDNA | |
| | Ct value | Tm value | Ct value | Tm value | Ct value | Tm value | Ct value | Tm value |
| $10^6$ | 36.90 | 83.75 | 35.44 | 83.59 | 36.14 | 84.02 | 24.23 | 84.00 |
| | 37.39 | 83.82 | 35.66 | 83.65 | — | — | 24.23 | 83.92 |
| $10^5$ | 35.38 | 83.66 | 33.26 | 83.63 | 37.38 | 83.73 | 24.24 | 83.76 |
| | 33.61 | 83.66 | 33.51 | 83.68 | 34.62 | 83.78 | 24.40 | 83.70 |
| $10^4$ | 31.90 | 83.68 | 32.45 | 83.56 | 31.47 | 83.81 | 24.12 | 83.69 |
| | 31.96 | 83.67 | 31.47 | 83.73 | 32.21 | 83.84 | 24.10 | 83.67 |
| $10^3$ | 28.46 | 83.76 | 28.32 | 83.72 | 29.11 | 83.88 | 23.87 | 83.67 |
| | 28.19 | 83.76 | 28.21 | 83.77 | 29.03 | 83.95 | 23.95 | 83.64 |
| $10^2$ | 25.04 | 83.59 | 24.90 | 83.62 | 25.28 | 83.88 | 22.81 | 83.55 |
| | 24.73 | 83.60 | 24.80 | 83.72 | 25.41 | 83.92 | 22.69 | 83.53 |
| 10 | 20.97 | 83.45 | 22.40 | 83.41 | 21.38 | 83.62 | 19.94 | 83.36 |
| | 20.78 | 83.49 | 22.45 | 83.54 | 21.28 | 83.71 | 19.73 | 83.36 |
| 1 | 19.47 | 83.36 | 19.81 | 83.38 | 20.21 | 83.62 | 17.55 | 83.28 |
| | 19.29 | 83.38 | 19.91 | 83.45 | 20.42 | 83.59 | 17.31 | 83.26 |

TABLE 8

| | | R2 | Standard curve |
|---|---|---|---|
| EMA treatment | Living cells + λDNA | 0.989 | Y = –3.128*LOG(X) + 18.76 |
| | Living cells + Dead cells + λDNA | 0.988 | Y = –2.718*LOG(X) + 19.89 |
| | Living cells + Dead cells | 0.967 | Y = –3.070*LOG(X) + 19.49 |
| No EMA treatment | Living cells + Dead cells + λDNA | 0.773 | Y = –1.098*LOG(X) + 19.08 |

As seen from Table 7, when a certain amount of a suspension of dead cells was added to the specimen solutions that were not treated with EMA and that were diluted with dilution rates higher than $10^3$ times, almost the same Ct values were obtained, indicating that the addition of λDNA did not vary the Ct value. As seen from Table 7, in the specimen solutions treated with EMA, the Ct values reflected the amount of living cells regardless of the addition of a suspension of dead cells. Thus, the EMA treatment probably suppressed the amplification of dead cell DNA as a template. In addition, as seen from the numerical values of R2 in Table 8, the correlation coefficient was improved by the addition of a nucleotide in the treatment with EMA, and it was found that a low amount of template could be quantitatively detected. Moreover, the Tm analytical values of the amplified products were all in the range of 83.6±0.5, and it was confirmed that any non-specific amplification did not occur in this study.

Example 6

Effect of Nucleotides

Using an *E. coli* genomic DNA sample to which dNTP was added as a nucleotide, EMA treatment was performed and detection sensitivities were compared by a real-time PCR method targeting a LacZ gene or 16SrDNA.

(1) Preparation of Samples

Genomic DNA prepared from *E. coli* K-12 was serially 10-fold diluted with TE buffer and adjusted to $1 \times 10^8$ to $1 \times 10^5$ copies/40 µL, and thereto were added the following nucleotides to obtain specimen solutions: a specimen solution to which each 250 µmol or each 125 µmol of dATP, dTTP, dCTP, and dGTP (manufactured by Takara Bio Inc., Catalog Number: 4026-4029) (total weight of deoxynucleotide triphosphate: 1000 µmol or 500 µmol) were added; a specimen solution to which 500 µmol of any one of the above-mentioned 4 deoxynucleotide triphosphates was added; a specimen solution to which each 250 µmol of dATP and dGTP were added; and a specimen solution as a control to which dNTP was not added.

All of the above-mentioned specimen solutions were adjusted to 50 µL with sterile water and used in the treatment (2) described below.

(2) EMA Treatment

Each specimen solution prepared in Example 6-(1) was treated with EMA only once in the same manner as in Example 4-(2) except that 5 µL of an aqueous EMA solution was added.

Further, a specimen solution which was prepared as described in Example 6-(1) except that the EMA treatment was not performed was prepared. The specimen solutions with EMA treatment and the specimen solutions without EMA treatment were diluted to 100 µL with sterile water.

(3) PCR Targeting LacZ Gene or 16SrDNA

A PCR reaction solution (total volume 20 µL) with the following composition was prepared.
  SYBR Premix Ex Taq (manufactured by Takara Bio Inc., catalog number: RR041A): 10 µL
  Forward primer: 1 µL
  Reverse primer: 1 µL
  Sterile water: 7 µL
  Template DNA (the diluted specimen solution): 1 µL Herein, the forward and reverse primers were added to the PCR reaction solution in the following three combinations.

(A) Combination to Amplify a Part (70 bp) of the LacZ Gene
  4 pmol/µL, LazZ-F DNA (Sequence ID NO 1): 1 µL
  4 pmol/µL, LacZ-R DNA (Sequence ID NO 2): 1 µL (B) Combination to Amplify a Part (177 bp) of the LacZ Gene
  4 pmol/µL, LazZ-F DNA (Sequence ID NO 1): 1 µL
  4 pmol/µL, LacZ-R_177 DNA (SEQ ID NO 3): 1 µL (C) Combination to Amplify a Part (95 bp) of 16SrDNA 8 pmol/μL, 16S-F_95 DNA (SEQ ID NO 4): 1 μL
8 pmol/μL, 16S-R DNA (SEQ ID NO 5): 1 μL Each specimen solution (1 μL) prepared in Example 6-(2) was used as a template DNA. That is, 20 μL of the reaction solution contains $10^6$ to $10^3$ copies of *E. coli* genome as a template DNA. The PCR was performed in the same manner as in Example 4-(3) except for the above.

(4) Test Results

For the Ct values and Tm analytical values obtained by PCR in Example 6-(3), the results of the primer pairs (A) are shown in Table 9, the results of the primer pairs (B) are shown in Table 10, and the results of the primer pairs (C) are shown in Table 11 and Table 12. Herein, the symbol "-" in the Table indicates that the amplification of the LacZ gene or 16SrDNA by PCR was not detected.

TABLE 9

| | EMA treatment | | | | | | No EMA treatment | | | |
|---|---|---|---|---|---|---|---|---|---|---|
| | No addition of dNTPs | | Addition of dNTPs (250 μmol each) | | Addition of dNTPs (125 μmol each) | | No addition of dNTPs | | Addition of dNTPs (250 μmol each) | |
| Copy number | Ct value | Tm value | Ct value | Tm value | Ct value | Tm value | Ct value | Tm value | Ct value | Tm value |
| $10^6$ | 28.94 | 83.03 | 32.76 | 83.07 | 32.29 | 82.97 | 18.25 | 83.19 | 18.38 | 83.17 |
| | 28.85 | 83.16 | 32.59 | 83.08 | 33.53 | 82.97 | | | | |
| | 28.85 | 83.21 | 32.44 | 83.07 | 33.18 | 83.00 | | | | |
| $10^5$ | | | Not performed | | | | 21.61 | 83.21 | 21.74 | 83.17 |
| $10^4$ | | | | | | | 25.00 | 83.24 | 25.23 | 83.20 |
| $10^3$ | | | | | | | 28.34 | 83.23 | 28.75 | 83.19 |

TABLE 10

| | EMA treatment | | | | | | No EMA treatment | | | |
|---|---|---|---|---|---|---|---|---|---|---|
| | No addition of dNTPs | | Addition of dNTPs (250 μmol each) | | Addition of dNTPs (125 μmol each) | | No addition of dNTPs | | Addition of dNTPs (250 μmol each) | |
| Copy number | Ct value | Tm value | Ct value | Tm value | Ct value | Tm value | Ct value | Tm value | Ct value | Tm value |
| $10^6$ | — | — | — | — | — | — | 17.74 | 85.38 | 17.86 | 85.41 |
| | 35.86 | 85.61 | — | — | — | — | | | | |
| | — | — | — | — | — | — | | | | |
| | 36.16 | 85.66 | — | — | — | — | | | | |
| $10^5$ | | | Not performed | | | | 21.09 | 85.38 | 21.29 | 85.34 |
| $10^4$ | | | | | | | 24.70 | 85.39 | 25.12 | 85.42 |
| $10^3$ | | | | | | | 28.02 | 85.42 | 28.41 | 85.53 |

TABLE 11

| | EMA treatment | | | | | |
|---|---|---|---|---|---|---|
| | No addition of each dNTPs | | Addition of dNTPs (125 μmol each) | | Addition of dATP + dGTP (250 μmol each) | |
| Copy number | Ct value | Tm value | Ct value | Tm value | Ct value | Tm value |
| $10^6$ | 28.90 | 82.23 | 34.93 | 82.10 | 34.04 | 82.23 |
| | 28.82 | 82.26 | 34.97 | 82.15 | 35.85 | 82.11 |
| | 28.25 | 82.24 | 34.46 | 82.22 | 34.99 | 82.17 |
| | 28.73 | 82.32 | 34.81 | 82.28 | 34.93 | 82.14 |

TABLE 12

| | EMA treatment | | | | | | | |
|---|---|---|---|---|---|---|---|---|
| | dATP (500 μmol) | | dGTP (500 μmol) | | dCTP (500 μmol) | | dTTP (500 μmol) | |
| Copy number | Ct value | Tm value | Ct value | Tm value | Ct value | Tm value | Ct value | Tm value |
| $10^6$ | 32.18 | 82.11 | 36.26 | 82.07 | 30.03 | 82.12 | 30.22 | 82.23 |
| | 32.50 | 82.15 | 36.14 | 81.96 | 30.05 | 82.22 | 30.17 | 82.25 |
| | 32.78 | 82.13 | 36.04 | 82.06 | 30.14 | 82.22 | 30.21 | 82.28 |
| | 32.53 | 82.23 | 35.25 | 82.16 | 30.19 | 82.27 | 30.17 | 82.34 |

As seen from Tables 9 and 10, in the case of no treatment with EMA, no difference was observed in the Ct values with or without the addition of dNTPs and the Ct values were decreased depending on the copy number of the template. Thus, it was confirmed that the addition of dNTPs did not affect PCR. Further, the treatment with EMA increased the Ct value by about 10 cycles as compared with the case of no treatment with EMA, and the addition of nucleotides further increased the Ct value by 4 to 5 cycles or made the amount of the amplified product lower than or equal to the detection limit. Thus, the addition of a nucleotide(s) probably promoted the DNA modification with EMA, resulting in reduction of the PCR efficiency. As seen from Table 11 and Table 12, the same results were obtained for the detection of 16SrDNA. Thus, it was found that the treatment with EMA following the addition of a nucleotide(s) promoted the modification of template DNA regardless of the kinds of the added nucleotide(s). Herein, the Tm analytical values of the amplified products were 83.0±0.5 for the primer pair (A), 85.5±0.5 for the primer pair (B), and 82.0±0.5 for the primer pair (C), and there was no difference among the specimen solutions.

INDUSTRIAL APPLICABILITY

According to the present invention, nucleic acid modification efficiency can be increased in the treatment of bringing a sample into contact with a nucleic acid-modifying agent. Therefore, the present invention provides a method of selectively detecting a nucleic acid of a living cell with a high sensitivity, and a kit and a composition used for the method. Thus, the present invention is extremely useful for increasing the accuracy of food hygiene inspection and clinical testing.

SEQUENCE LISTING FREE TEXT

SEQ ID NO: 1: Nucleotide sequence of LacZ-F
SEQ ID NO: 2: Nucleotide sequence of LacZ-R
SEQ ID NO: 3: Nucleotide sequence of LacZ-R_177
SEQ ID NO: 4: Nucleotide sequence of 16S-F_95
SEQ ID NO: 5: Nucleotide sequence of 16S-R

The invention claimed is:
1. A composition comprising:
(a) a nucleic acid-modifying agent,
(b) an acidic polysaccharide; and
(c) a nucleic acid,
wherein the nucleic acid-modifying agent is a compound capable of modifying a nucleic acid by photoactivation,
wherein the composition is a solution, and
wherein the acidic polysaccharide is selected from sodium alginate and chondroitin sulfate B, and the nucleic acid-modifying agent is a compound selected from ethidium monoazide and propidium monoazide.

* * * * *